(12) United States Patent
Killeen et al.

(10) Patent No.: US 9,880,154 B2
(45) Date of Patent: *Jan. 30, 2018

(54) METHOD FOR SCREENING DRUGS AND ANIMAL MODEL FOR SAME

(71) Applicants: William T Killeen, Fairfield, FL (US); Siobhan Ellison, Fairfield, FL (US)

(72) Inventors: William T Killeen, Fairfield, FL (US); Siobhan Ellison, Fairfield, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/120,462

(22) Filed: May 20, 2014

(65) Prior Publication Data
US 2015/0338394 A1   Nov. 26, 2015

(51) Int. Cl.
G01N 33/50     (2006.01)
G01N 33/569    (2006.01)
G01N 33/94     (2006.01)

(52) U.S. Cl.
CPC ... G01N 33/5088 (2013.01); G01N 33/56905 (2013.01); G01N 33/944 (2013.01); G01N 2333/44 (2013.01); G01N 2469/20 (2013.01)

(58) Field of Classification Search
CPC ......... G01N 33/5088; G01N 33/56905; G01N 33/944
See application file for complete search history.

(56) References Cited

U.S. PATENT DOCUMENTS

2014/0045885 A1*  2/2014  Ellison .................. 514/312

OTHER PUBLICATIONS

Ellison and Lindsay. Intern J Appl Res Vet Med 10(1):1-7, 2012.*
Ho et al. Analytica Chimica Acta 638:58-68, 2009.*
Dubey and Lindsay. International Journal of Parasitology 28:1823-1828, 1998.*
USDA website dated Aug. 13, 2016. Printed from www.ars.usda.gov/northeast-area/Beltsville-agricultural-research-center/animal-parasitic-diseases-laboratory/docs/epmsarcocystis-neurona. pp. 1-3.*
Ong et al. PLOS Pothogens 9(6):e1003444, 2013. pp. 1-11.*

* cited by examiner

Primary Examiner — Marcia S Noble

(57) ABSTRACT

Acetylcholine and its receptors appeared in evolution before development of a nervous system. Cholinergic agonists functions include proliferation, differentiation, and cell-to-cell contact in protozoa] as well as vertebrate cells. Animal models for infection by Apicomplexan parasites require cell-to-cell contact followed by differentiation of parasite and host cells to produce clinical disease. Experimental infections are produced by introducing parasite infected leukocytes into a host. Binding cholinergic receptors on the parasites and leukocytes with levamisole HCl induces non-progressive infections and absence of signs of disease.

8 Claims, No Drawings

METHOD FOR SCREENING DRUGS AND ANIMAL MODEL FOR SAME

FIELD

The present invention concerns prolonging parasitemia without inducing clinical signs of disease by binding cholinergic receptors on parasites and leukocytes. Ligation of acetylcholine binding sites by levamisole HCl can induce allosteric transitions sufficient for receptor signaling in Apicomplexan parasites and mammalian leukocytes. Cholinergic receptor signaling is involved in the pathogenesis of apicomplexan disease. An animal model for human and non-human neurologic disease and dysfunction, and particularly relating to Apicomplexan parasites including but not limited to *Sarcocystis neurona, Sarcorystis dasypus* (syn. *S. neurona*), *Sarcorystis cruzi, Sarcocystis falcatula, Sarcocystis* sp., *Toxoplasma gondii, Neospora caninum, N. hughesi, Eimeria* and *Plasmodium* is created by administration of levamisole HCl to an infected host.

BACKGROUND

The development of effective treatments, therapies or diagnostics for Apicomplexan parasite diseases has been hampered by lack of suitable models for study. Apicomplexans are parasitic protozoa that modulate host immune systems to favor infection of the host. It is known that Trypanosomes bind to muscarinic cholinergic receptors of host cells and attenuate secretion of immune regulator effector molecules. Identification of receptors and their ligands used by parasitic protozoa are important for understanding disease.

Apicomplexan parasites such as *Sarcorystis neurona* also cause disease by manipulating immune effector molecules, cytokines, that facilitate infections. Illustratively, Equine Protozoal Myeloencephalitis (EPM) which is the leading infectious neurologic equine disease in the Western Hemisphere is caused by the Apicomplexan parasite *Sarcorystis neurona* (*S. neurona*). The signs of disease caused by *S. neurona* are related to neuroinflammation. In most cases the parasite is no longer evident in the hosts central nervous system during chronic disease. Cytokine mediated inflammation is the predominantly recognized lesion. There is an intricate relationship between parasite invasion of leukocytes and cytokine responses to infection that dramatically impact expression of parasite genes. Parasite induced host cell cytokines drive proinflammatory responses and these responses may regulate genes that regulate parasite stage conversion in the host.

While the symptoms and effects of EPM have been recognized since the 1970's, it was not until 1991 that the protozoan parasite that causes EPM was isolated and cultured from a horse and given the name *Sarcorystis neurona*. *Sarcorystis neurona* cycles naturally between opossums and armadillos/raccoons. The feces of the opossum (the definitive host) is likely the source of the infection for horses. Thus, the horse is an aberrant host, becoming exposed when it consumes infectious material from opossum feces. In the horse, the most prominent EPM-producing organism, *S. neurona*, does not produce clinical signs of disease as a result of cyst formation, but as the cysts (sporozoites) convert to merozoites which in turn stimulate leukocytes that release cytokines in response to the infection. These cytokines can cross the blood brain barrier where they are proinflammatory. Clinical signs in a horse with EPM do not develop until the merozoite interacts with a functional white blood cell stimulating release of molecules that are responsible for inflammation.

The importance of leukocytes in the pathogenesis of sarcocystosis is evident by experiment. Severe combined immunodeficient (SCID) foals supported prolonged visceral infections and a parasitemia (from ingestion of *S. neurona* sporocysts) but did not develop clinical signs of EPM. Merozoite challenge (IV) using *S. neurona* also produced prolonged visceral infections without clinical signs of EPM in SCIO foals. In these SCIO foals (the absence of functional leukocytes) parasites did not enter the CNS despite the persistence of infections. Infection challenge of immunocompetent foals with *S. neurona* sporocysts result in a rapidly controlled parasitemia followed by clinical signs but no parasites enter the CNS. From the foregoing, it is evident that the interplay between the leukocyte and parasite are necessary to allow parasite stage conversion (to a stage that can enter the CNS via a leukocyte) and production of innate immune responses responsible for neuroinflammation.

Serum cytokines are the products of immune reaction to parasitic protozoa. Cytokines can cross the blood brain barrier within the central nervous system where they are proinflammatory. In an immunocompetent horse, the initial merozoite stage resulting in a parasitemia is quickly controlled. Some merozoites enter leukocytes and are transported to the CNS and can cause lesions in these tissues. Often parasites are not found in the CNS but neuroinflammation is recognized on histopathological examination.

Neuroinflammation is recognized in. the clinically ill animal. These signs include weakness, muscle atrophy, spinal ataxia, or "wobbling" and/or head tilt with asymmetry of the face (e.g., eyelid, ear, or lip). A severely EPM-affected horse may go down and be unable to rise. Lameness not traceable to orthopedic disease or any combination of the above signs may occur in early or less severe infections. In most cases, an affected horse is bright and alert with a normal appetite, hematological and biochemical blood values are usually in the normal range.

Epidemiology and economic significance of *S. neurona* infection is substantial. Of animals clinically affected, 30-40% reportedly fail to respond to current therapy, and some of these animals die. Conventional therapy relies on drug/medications and/or combinations that target organelles specific to protozoa. The efficacy of treatments cannot be optimized because of the lack of a model of the disease that can define molecular targets. Better and more effective prophylactic, or therapeutic modalities are required but were not thoroughly investigated before an animal model predictably produced disease. Unexpectedly, binding cholinergic receptors using levamisole HCl in the autologous leukocyte model of infection induced a parasitemia with no clinical signs as observed in the SCID infection experiment. Such a method can be used to identify molecular targets that are the progenitors of disease induced by *S. neurona* and will be applicable to other apicomplexans that cause neuroinflammation.

There are other animal induced infection models for *S. neurona*. An infection of nude mice or interferon gamma knock-out mice with sporocysts or culture derived merozoites produced infections. These experiments result in neurological signs and isolation of the organism from the CNS. However, the relevancy of this model is doubtful since these mice are immune-deficient; thus any immune-based selection forces acting in normal animals are absent. Similarly the model that used SCID foals that supported prolonged visceral infections and a parasitemia (from ingestion of *S.*

*neurona* sporocysts) but did not develop clinical signs of EPM suffer because immune based selection forces acting in normal animals are absent. One animal model, which has been used to date to study *S. neurona* isolated from natural cases of EPM, uses autologous leukocytes that have been previously infected in vitro with *S. neurona*. This Trojan Horse model produces clinical signs and allows parasites to enter the CNS of horses (as was shown by culture).

From the foregoing, it would be realized that despite a great deal of past and on-going effort, there remains an unfulfilled need for animal models for Apicomplexan parasitic diseases that induce neuroinflammation.

SUMMARY

In accordance with the foregoing, the present invention encompasses an animal model for investigating neurological disease. The present invention exploits the discovery that levamisole HCl is highly active against apicomplexan merozoites apparently blocking their entry into leukocytes. Further, it is a novel discovery that levamisole HCL even at low concentrations accomplishes the modulation of the immune system preventing the release of proinflammatory cytokines that are agents of disease. According to the invention, levamisole HCl, an imidazothiazole, and its derivatives, act as cholinergic agonists by binding physiologically functional receptors on apicomplexan parasites and host leukocytes. Therefore, levamisole given to a mammal will prevent clinical signs of neuro encephalitis by altering innate immune functions that facilitate parasitic protozoal disease.

In order to accomplish these and other objects of the invention, the present invention in a preferred embodiment provides a method of blocking disease by limiting a critical step in infection. An apicomplexan parasite which is incorporated in a host cell, such as a leukocyte cell from an immunocompetent host, in an amount that is effective to cross the brain or placental barrier of the host, when the host is inoculated with the parasite-incorporated cell is used. The present invention is directed to a unique discovery that mammalian cells, specifically leukocytes of all types and any other cell that can be activated so as to cross the blood brain barrier or the placental barrier, can be infected by merozoites of apicomplexan organisms and progression of the infection can be limited to the blood stage with cholinergic agonists that act on either leukocytes, or parasites, or both.

The results of the model are that after merozoite infection of the mammalian cells, the infected cells are introduced into mammals, producing a parasitemia. A prolonged parasitemia in an immunocompetent host allows tagging and isolation of specific levamisole sensitive receptors. Targeting a single receptor, as was shown in the SCID foals, renders one aspect of functional leukocytes incapable of transmitting infection and disease. The novel invention targets levamisole sensitive cholinergic receptors by its ligand in order to elucidate the pathogenesis of apicomplexan disease such as leukocyte adherence. Surprisingly, it was also discovered that targeting levamisole sensitive cholinergic receptors by its ligand prevented clinical signs of disease. It is recognized that Trypanosome membrane attachment to muscarinic cholinergic receptors results in attenuation of secretion of prostaglandin E2-prostaglandin E2 is an immune regulator effector. It is anticipated that other acetylcholine receptors are likely to function in parallel with levamisole sensitive receptors to mediate cholinergic immune responses. However, in the case of *S. neurona* infections binding levamisole sensitive cholinergic receptors alone are sufficient to ameliorate clinical signs of disease.

Models using apicomplexan parasites are required for development of efficacious drug treatments, prophylactic modalities such as drugs and vaccines, and diagnostic tests for determination of Apicomplexan infections. Apicomplexan diseases described by the present invention include but are not limited to Sarcocystosis, Toxoplasmosis, Malaria, and Neosporosis.

In another preferred embodiment, the invention provides a method of treating neurological disease or dysfunction, comprising administration to an animal or avian a biologically effective dose of an agent selected from the group consisting of acetylcholine agonists such as levamisole HCl, an imidazothiazole, and derivatives thereof.

In a further embodiment of such an inventive method; the neurological disease or dysfunction may be associated with infection with an apicomplexan parasite but due to stimulated host cell immune mediated molecules such as cytokines. The apicomplexan parasite may be *Sarcocystis neurona, Sarcorystis darypus* (syn *S. neurona*), *Sarcocystis cruzi, Sarcocystis falcatula, Sarcocystis* sp., *Toxoplasma gondii Neospora caninum, N. hughesi, Eimeria* and *Plasmodium*.

In a further preferred embodiment, the invention provides a method used when an infected host has been treated with an anti-protozoal and continues to suffer from immune mediated inflammation by administration of an acetylcholine agonists such as levamisole HCl.

More specifically, the present invention is directed to an animal model for *S. neurona* that produces infection in the blood of horses and ameliorates the clinical signs of EPM. Without being bound to any particular theory of the invention, this model is based on the discovery that virulent merozoite cells of *S. neurona* can be induced to enter certain mammalian cells cultured in vitro and they can be transferred back to the homologous host. After transfer, the homologous host cells infected with virulent merozoite cells migrate via the blood to the central nervous system and can cross the blood brain barrier. However, using a compound that can bind cholinergic receptors, specifically levamisole-like receptors, on the host cells and parasites, prevent the progression of disease. The clinical signs of disease are not induced by the virulent merozoites nor do the host cells produce cytokines that can induce the production of inflammatory molecules that traverse the blood brain barrier in response to the infection. In addition to preventing the clinical signs, an animal model provided as described will produce serum antibodies against the same EPM-producing organism and provide for demonstration of the organism from the blood tissues by staining or PCR.

It is a distinct feature of the present invention that specific mammalian cells are infected in vitro with an EPM-producing parasite, allowed to reach the stage of growth in which the merozoite stage of the parasite is optimally virulent, and is blocked from inducing clinical signs. It is also a distinct feature of the invention that it has now been recognized that the Apicomplexan parasites can evade the immune response and to produce clinical signs of disease and these reactions can be blocked by drug therapy thereby preventing disease.

The foregoing and other objects, aspects and advantages will be better understood from the following detailed description of the preferred embodiments of the infection.

DETAILED DESCRIPTION

Production of Persistent Parasitemia in a Horse:

In a first preferred embodiment a parasite population was isolated from horses as described in an experimental model (Experimental infection of horses with culture derived *Sarcocystis neurnoa* merozoites as a model for equine protozoal myeloencephalitis, 2004) and used to infect a yearling thoroughbred filly. The challenge (6000 organisms/day) was used daily for 10 days. Concurrent with the challenge infection the filly was administered 1 mg/kg levamisole HCl orally for 21 days. The serum antibody titer to SAG 1, 5, 6 was negative at 2 for each antigen at the onset of challenge. Daily blood samples were taken and 5 microliters of blood were used to prepare thin layer smears followed by staining with Geimsa. Ten fields were counted to determine the presence of *S. neurona*. A hemocytometer was used to determine the number of parasites per ml of peripheral blood. Day 10, the filly had no clinical signs and a parasitemia of one million organisms in the serum. At day 14, the filly had no clinical signs of disease and a parasitemia of one million organisms. At the end of fourteen days the filly was treated with decoquinate orally at 0.5 mg/kg for 10 days. At day 30, the horse had no visible parasites in the blood and no clinical signs of disease. It was previously established that infection for 10 days without the additional of levamisole HCl reliably results in clinical signs of disease in 93% of horses by day 30.

Modulating Cytokine Responses in Horses Using Levamisole HCl:

Field cases of idiopathic encephalitis associated with EPM due to *S. neurona* were identified by veterinary clinical examination. In a one-year period (2013), 54 horses received levamisole HCl at 1 mg/kg for signs of EPM that had not resolved with conventional treatment as indicated on submission forms for serum antibody analysis. Signs were assessed by the Field Veterinarian by a neurological examination of gait and scored on a scale of 1-5. Attributable data was obtained from 27 Field Veterinarians. Thirty-three animals were included into the study, missing data from 21 horses prevented inclusion of these 21 animals into the study analysis. In the included data set, one Field Veterinarian submitted data for 6 animals, one Field Veterinarian submitted data from two animals, and 25 veterinarians submitted data for one animal.

Horses were evaluated for a change in gait score by subtracting the gait score after treatment from the gait score before treatment. Twenty-seven (82%) of the horses had a gait score that improved by at least one grade after levamisole HCl treatment determined by veterinary neurological examination. The change in gait score ranged from 1 to 3 in this group. Six animals (18%) had a gait score that was worse or did not change after treatment. The change in gait score ranged from −2 to 0 in this group.

The results of this study indicate that 82% of horses showed a potential clinical benefit by alleviation of neuro inflammation when treated with levamisole HCl. Horses had not improved before treatment and had shown clinical decline that prompted veterinary attention. The positive treatment response in this study suggests that EPM treatment failures are due to a lack of recognition of an associated inflammatory condition that is levamisole responsive.

The following experimentation was conducted for the pharmacokinetics of levamisole HCl in horses:

Levamisole HCl is rapidly metabolized in horses. Horses given 5 mg/kg of levamisole HCl (2800 mg) orally reportedly have 485 ng/ml in plasma at one hour. In order to determine the plasma concentrations of low dose levamisole HCl three horses were given a single treatment. In this experiment adult male horses were given 550 mg, 1650 mg, or 2750 mg of levamisole HCl orally (1 mg/kg, 3 mg/kg, and 5 mg/kg). The plasma levels measured at 15 minutes were 606, 591, and 1082 ng/ml in plasma respectively. At one hour the plasma levels were 139, 690, and 750 ng/ml. The rapid elimination of levamisole HCl from plasma in horses may indicate that secondary messengers are responsible for the immune modulating effects apparent with treatment. Binding of levamisole to levamisole sensitive receptors are anticipated to increase cGMP, attenuation of CAMP, and attenuation of proinflammatory molecules that are immune regulating effectors.

While the invention above has been discussed with particular reference to horses, it will be appreciated that the invention is not particularly limited and may be used for other animals such as, by way of non-limiting examples, people, sea otters, sea lions, skunks, raccoons, mink, and other animals in aquaria, zoos or farms.

While the invention has been described in terms of its preferred embodiments, those skilled in the art will recognize that the infection can be practiced with modification within the spirit and scope of the appended claims.

The present invention provides animal models for Apicomplexan infections including but not limited to *Toxoplasma, Plasmodium, Neospora*, and/or *Sarcocystis*.

The present invention provides the models for development of preventive and/or therapeutic agents (drugs and vaccines) by demonstrating their effectiveness against Apicomplexan infections such as *Toxoplasma, Plasmodium, Neospora*, and/or *Sarcocystis* by specific acetylcholine receptor binding.

The invention claimed is:

1. A method for screening a candidate drug for treating a disease in an equine host, the disease being caused by *Sarcocystis neurona*, comprising:

obtaining an equine host model that has been infected with *Sarcocystis neurona* and treated with a sufficient amount of a cholinergic agonist agent to prevent clinical signs of the disease caused by *Sarcocystis neurona* without killing the *Sarcocystis neurona*, thereby exhibiting a parasitemia in the equine model;

administering the candidate drug to the equine model; and determining whether the candidate drug reduces the parasitemia in the equine model.

2. The method of claim 1, wherein the cholinergic agonist agent is levamisole HCL, imidazothiazole, salts thereof, esters thereof or derivatives thereof.

3. The method of claim 1, wherein the cholinergic agonist is administered by a route selected from the group consisting of: oral, intranasal, topical, inhalation, intravenous injection, intramuscular injection, subcutaneous injection, intraperitoneal injection, intratracheal injection, intrathecal injection and combinations thereof.

4. The method of claim 1 wherein the dose of cholinergic agonist agent used to obtain a parasitemia in the mammalian host is between 0.001 and 100 mg/kg.

5. The method of claim 1, wherein the dose of cholinergic agonist agent used to obtain a parasitemia in the equine host is between 0.1 and 10 mg/kg.

6. The method of claim 1, wherein the dose of cholinergic agonist agent used to to obtain a parasitemia in the equine host is 1 mg/kg.

7. The method of claim 1, wherein the dosage form of the cholinergic agonist agent is a member selected from the group consisting of a powder, a solid, a liquid, a crystal, a pill, a tablet, a capsule, a thin film, a suspension, a paste, a cream, a gel, a liniment, a balm, a lotion, an ointment, and a skin patch.

8. The animal model as described in claim 1.

\* \* \* \* \*